United States Patent
Suga et al.

(10) Patent No.: US 9,107,583 B2
(45) Date of Patent: Aug. 18, 2015

(54) OPTICAL MEASUREMENT PROBE

(71) Applicant: OLYMPUS MEDICAL SYSTEMS CORP., Tokyo (JP)

(72) Inventors: Takeshi Suga, Hino (JP); Kenji Kamimura, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 13/742,441

(22) Filed: Jan. 16, 2013

(65) Prior Publication Data

US 2013/0211262 A1 Aug. 15, 2013

Related U.S. Application Data

(63) Continuation of application No. PCT/JP2012/065429, filed on Jun. 15, 2012.

(60) Provisional application No. 61/508,387, filed on Jul. 15, 2011.

(51) Int. Cl.
*A61B 5/00* (2006.01)
*G01N 21/47* (2006.01)
*A61B 1/00* (2006.01)
*A61B 1/07* (2006.01)
*A61B 1/018* (2006.01)

(52) U.S. Cl.
CPC ........... *A61B 5/0084* (2013.01); *A61B 1/00165* (2013.01); *A61B 1/07* (2013.01); *A61B 5/0082* (2013.01); *G01N 21/474* (2013.01); *A61B 1/018* (2013.01); *G01N 2021/4742* (2013.01)

(58) Field of Classification Search
USPC .......................................... 600/473, 476, 478
See application file for complete search history.

(56) References Cited

U.S. PATENT DOCUMENTS

| | | | |
|---|---|---|---|
| 5,034,010 A * | 7/1991 | Kittrell et al. ................. | 600/478 |
| 5,926,262 A | 7/1999 | Jung et al. | |
| 6,404,497 B1 | 6/2002 | Backman et al. | |
| 6,503,196 B1 | 1/2003 | Kehr et al. | |
| 2003/0231309 A1 | 12/2003 | Fulghum, Jr. et al. | |

(Continued)

FOREIGN PATENT DOCUMENTS

| | | |
|---|---|---|
| DE | 1 974 3431 A1 | 4/1999 |
| EP | 0 549 097 A1 | 6/1993 |

(Continued)

OTHER PUBLICATIONS

Utzinger et al. "Fiber optic probes for biomedical optical spectroscopy". Journal of Biomedical Optics 8(1), pp. 121-147 (Jan. 2003).*

(Continued)

*Primary Examiner* — Unsu Jung
*Assistant Examiner* — Phong K Huynh
(74) *Attorney, Agent, or Firm* — Oliff PLC

(57) ABSTRACT

A probe includes a plurality of optical fibers that includes an irradiation fiber and a light-receiving fiber; and an optical member of which a base end face is arranged to abut on leading end faces of the optical fibers, and a leading end face is exposed to an outer side. The leading end face of the optical member is perpendicular to a longitudinal direction of the probe. Light emitted from the irradiation fiber passes through a path inclined with respect to a perpendicular line of the leading end face.

3 Claims, 14 Drawing Sheets

(56) References Cited

U.S. PATENT DOCUMENTS

2003/0232445 A1 12/2003 Fulghum, Jr.
2008/0037024 A1 2/2008 Backman et al.
2009/0009759 A1 1/2009 Backman et al.

FOREIGN PATENT DOCUMENTS

| JP | A-2000-515407 | 11/2000 |
|----|---------------|---------|
| JP | A-2002-508076 | 3/2002 |
| JP | A-2002-535027 | 10/2002 |
| JP | A-2002-535645 | 10/2002 |
| JP | A-2005-515472 | 5/2005 |
| JP | A-2005-515473 | 5/2005 |
| JP | A-2009-537014 | 10/2009 |
| WO | WO 98/05253 A1 | 2/1998 |
| WO | WO 00/43750 A2 | 7/2000 |
| WO | WO 2007/133684 A2 | 11/2007 |

OTHER PUBLICATIONS

Nieman et al. "Compact beveled fiber optic probe design for enhanced depth discrimination in epithelial tissues". Optics Express, vol. 17, Issue 4, pp. 2780-2796 (2009).*
Jul. 5, 2013 Office Action issued in Japanese Patent Application No. 2013-501953 (with translation).
International Search Report issued in International Patent Application No. PCT/JP2012/065429 dated Jul. 10, 2012 (w/ translation).
Japanese Office Action issued in Japanese Patent Application No. 2013-501953 dated Mar. 19, 2013 (w/ translation).
Jan. 29, 2015 European Search Report issued in European Patent Application No. 12814597.6.

* cited by examiner

OPTICAL MEASUREMENT PROBE

CROSS-REFERENCE TO RELATED APPLICATIONS

The present invention relates to a probe including a plurality of optical fibers of which at least leading end portions are arranged in parallel with each other and an optical member of which a base end face is arranged to abut on leading end faces of the plurality of optical fibers, and a leading end face is exposed outside the probe.

BACKGROUND OF THE INVENTION

1. Field of the Invention

The present invention relates to a probe including a plurality of optical fibers of which at least leading end portions are arranged in parallel with each other and an optical member of which a base end face is arranged to abut on leading end faces the optical fibers, and a leading end face is exposed externally.

2. Description of the Related Art

In recent years, there is known a measurement method for measuring an optical characteristic of body tissue while a probe leading end directly makes contact with body tissue by inserting a probe into a forceps channel of an endoscope for observing internal organs such as digestive organs and protruding the probe leading end from the endoscope.

For example, there has been proposed an optical measurement apparatus using low-coherence enhanced backscattering (LEBS) technique for detecting properties of body tissue by irradiating low-coherent white light having a short spatial coherent length from an irradiation fiber leading end of a probe onto body tissue and measuring an intensity distribution of scattering light beams having a plurality angles using a plurality of light-receiving fibers (for example, refer to International Patent Publication Pamphlet No. WO2007/133684 or U.S. Patent Application Laid-Open No. 2008/0037024). In such an optical measurement apparatus, a transparent rod is provided in the probe leading end, and a distance between leading end faces of respective fibers and body tissue as a measurement target is regularized to obtain stability of measurement (for example, refer to Japanese Laid-open Patent Publication No. 2002-535027). In addition, in the probe disclosed in Japanese Laid-open. Patent Publication No. 2002-535027, in order to prevent undesired light, which is reflected by the leading end face of the rod without reaching the body tissue, from reaching the light-receiving fiber, the leading end face of the rod is notched with an inclination relative to the longitudinal direction of the probe so that only the scattering light of the obtainment target is measured.

SUMMARY OF THE INVENTION

A probe according to an embodiment of the present invention includes a plurality of optical fibers that include an irradiation fiber and a light-receiving fiber; and an optical member of which a base end face is arranged to abut on leading end faces of the optical fibers, and a leading end face is exposed to an outer side. The leading end face of the optical member is perpendicular to a longitudinal direction of the probe. Light emitted from the irradiation fiber passes through a path inclined with respect to a perpendicular line of the leading end face.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
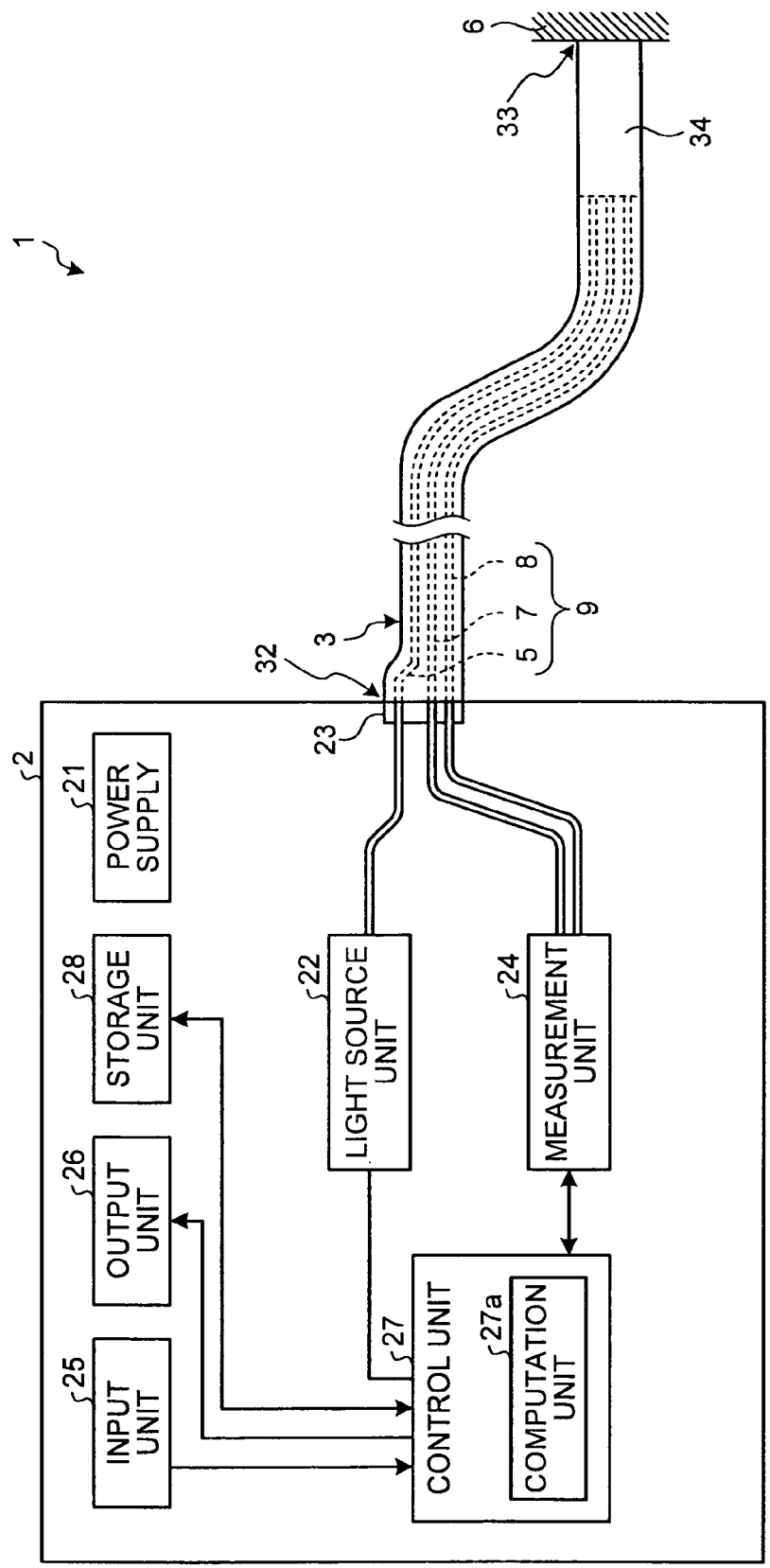
FIG. 1 is a schematic diagram illustrating a schematic configuration of an optical measurement apparatus according to a first embodiment.

Hereinafter, an optical measurement apparatus using the LEBS technique will be described in detail as exemplary embodiments of an optical measurement apparatus according to the invention with reference to the accompanying drawings. The invention is not limited to the embodiments described below. In the description of drawings, like reference numerals denote like elements. It is noted that the drawings are schematically provided, and thicknesses and widths of each element and ratios of each element may be different from those of the reality. Among the drawings, a portion having a different relationship or ratio from that of other drawings may be included.

First Embodiment

FIG. 1 is a schematic diagram illustrating a schematic configuration of an optical measurement apparatus according to a first embodiment of the invention. As illustrated in FIG. 1, the optical measurement apparatus 1 according to the first embodiment includes a main unit 2 that performs optical measurement for a body tissue 6 as a measurement target to detect properties of the body tissue 6 and a measurement probe 3 inserted into a subject. The probe 3 has flexibility. In the probe 3, a base end 32 is detachably connected to the main unit 2, and the light supplied, using the connected main unit 2, from the base end 32 is emitted to the body tissue 6 from a leading end 33. In addition, scattering light and reflection light as returned light from the body tissue 6 incident from the leading end 33 are output to the main unit 2 from the base end 32.

The main unit 2 includes a power supply 21, a light source unit 22, a connector 23, a measurement unit 24, an input unit 25, an output unit 26, a control unit 27, and a storage unit 28.

The power supply 21 supplies electric power to each element of the main unit 2.

The light source unit 22 outputs and generates light to be irradiated onto the body tissue 6. The light source unit 22 includes a light source as a low-coherent light source such as white light-emitting diode (LED) that emits white light, a xenon lamp, a halogen lamp or an LED and one more lenses (not illustrated). The light source unit 22 supplies low-coherent light to be irradiated onto a target to an irradiation fiber 5 of the probe 3 described below.

The connector 23 is used to detachably connect the base end 32 of the probe 3 to the main unit 2. The connector 23 supplies, to the probe 3, light emitted from the light source unit 22 and outputs, to the measurement unit 24, the returned light output from the probe 3.

The measurement unit 24 spectrometrically measures the light output from the probe 3 and returned from the body tissue 6. The measurement unit 24 includes a plurality of spectroscopic measurement devices. The measurement unit 24 measures spectral components and an intensity of the returned light output from the probe 3 to perform measurement for each wavelength. The measurement unit 24 outputs the measurement result to the control unit 27.

The input unit 25 is realized by a push-type switch and the like. The input unit 25 receives instruction information for instructing activation of the main unit 2 or other types of instruction information and inputs it to the control unit 27 by manipulating the switch and the like.

The output unit 26 outputs information regarding various types of processes in the optical measurement apparatus 1. The output unit 26 is realized by a display, a loudspeaker, a motor, and the like and outputs information regarding various processes in the optical measurement apparatus 1 using sound, images, vibration, and the like.

The control unit 27 controls processing operations of each element in the main unit 2. The control unit 27 is realized by a central processing unit (CPU) and a semiconductor memory such as a random access memory (RAM). The control unit 27 controls operations of the main unit 2 by transmitting instruction information or data to each element of the main unit 2 and the like. The control unit 27 causes the storage unit 28 to be described below to store the measurement result of the measurement unit 24 that has plural measuring devices. The control unit 27 has a computation unit 27a.

The computation unit 27a performs plural types of computation processes based on the measurement result of the measurement unit 24 to compute the characteristic value regarding properties of the body tissue 6. The type of the characteristic value as the characteristic value computed by the computation unit 27a and serving as an obtainment target is set depending on instruction information input from the input unit 25 by an operator's manipulation, for example.

The storage unit 28 stores an optical measurement program for executing the optical measurement process in the main unit 2 and various types of information regarding the optical measurement process. The storage unit 28 stores each measurement result from the measurement unit 24. In addition, the storage unit 28 stores the characteristic value computed by the computation unit 27a.

The probe 3 has the base end 32 detachably connected to the predetermined connector 23 of the main unit 2 and the leading end 33 that makes direct contact with the body tissue 6. The leading end 33 emits light supplied from the light source unit 22 and receives scattering light from a measurement target. In using the LEBS technique, the probe 3 is provided with a plurality of light-receiving fibers for respectively receiving at least two scattering light beams having different scattering angles. Specifically, the probe 3 has the irradiation fiber 5 that propagates light from the light source unit 22 supplied through the base end 32 and irradiates the light from the leading end 33 onto the body tissue 6, and two light-receiving fibers 7 and 8, each of which propagates scattering light and reflection light from the body tissue 6 incident from the leading end 33 and outputs the light to the base end 32. The irradiation fiber 5 and the light-receiving fibers 7 and 8 are provided as a fiber unit 9 to parallelize at least the leading end portions. The leading ends of the irradiation fiber 5 and the light-receiving fibers 7 and 8 are provided with a rod 34 having transparency as an optical member. The rod 34 has a cylindrical shape such that distances between the surface of the body tissue 6 and the leading ends of the irradiation fiber 5 and the light-receiving fibers 7 and 8 become constant. Although the probe 3 has two light-receiving fibers 7 and 8 in the example of FIG. 1, it is satisfactory if at least two or more scattering light beams having different scattering angles can be received, and thus the probe 3 may have three or more light-receiving fibers.

Figure 2:
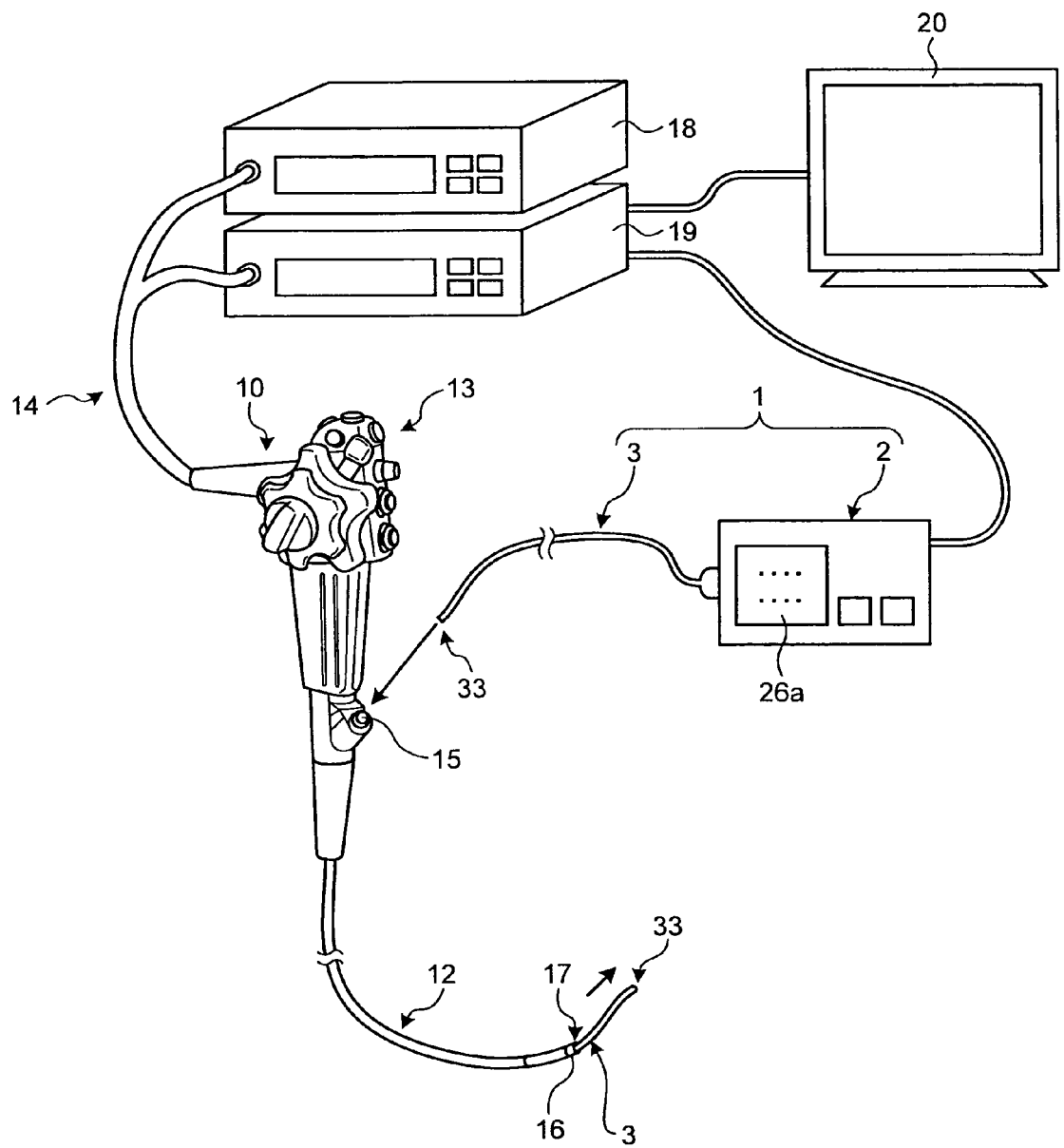
FIG. 2 is a diagram illustrating an endoscope system configuration and an installation state of a probe in the optical measurement apparatus.

The optical measurement apparatus 1 is usually combined with an endoscope system that observes internal organs such as digestive organs. FIG. 2 is a diagram illustrating a configuration of the endoscope system and an installation state of the probe 3 in the optical measurement apparatus 1. In FIG. 2, a flexible universal cord 14 extending from the lateral portion of a manipulation unit 13 is connected to a light source device 18 and a signal processing device 19 that processes a subject image captured in a leading end portion 16 of an endoscope 10. The signal processing device 19 is connected to a display 20. The display 20 displays various types of information regarding examination including the subject image processed by the signal processing device 19.

The probe 3 is inserted from a probe channel insertion hole 15 in the vicinity of the manipulation unit 13 of the out-body portion of the endoscope 10 inserted into an inner side of the subject. The leading end 33 of the probe 3 passes through an inner side of an insertion portion 12 and protrudes from an aperture 17 of the leading end portion 16 connected to the probe channel as indicated by the arrow. As a result, the probe 3 is inserted into an inner side of the subject to initiate the optical measurement.

A predetermined surface of the main unit 2 is provided with a display screen 26a for displaying a characteristic value computed by the computation unit 27a or the like, a switch included in a part of the input unit 25, and the like. As illustrated in FIG. 2, the main unit 2 of the optical measurement apparatus 1 and the signal processing device 19 may be connected to each other, and various types of information processed in the optical measurement apparatus 1 may be output to the signal processing device 19 and displayed on the display 20.

Figure 3:
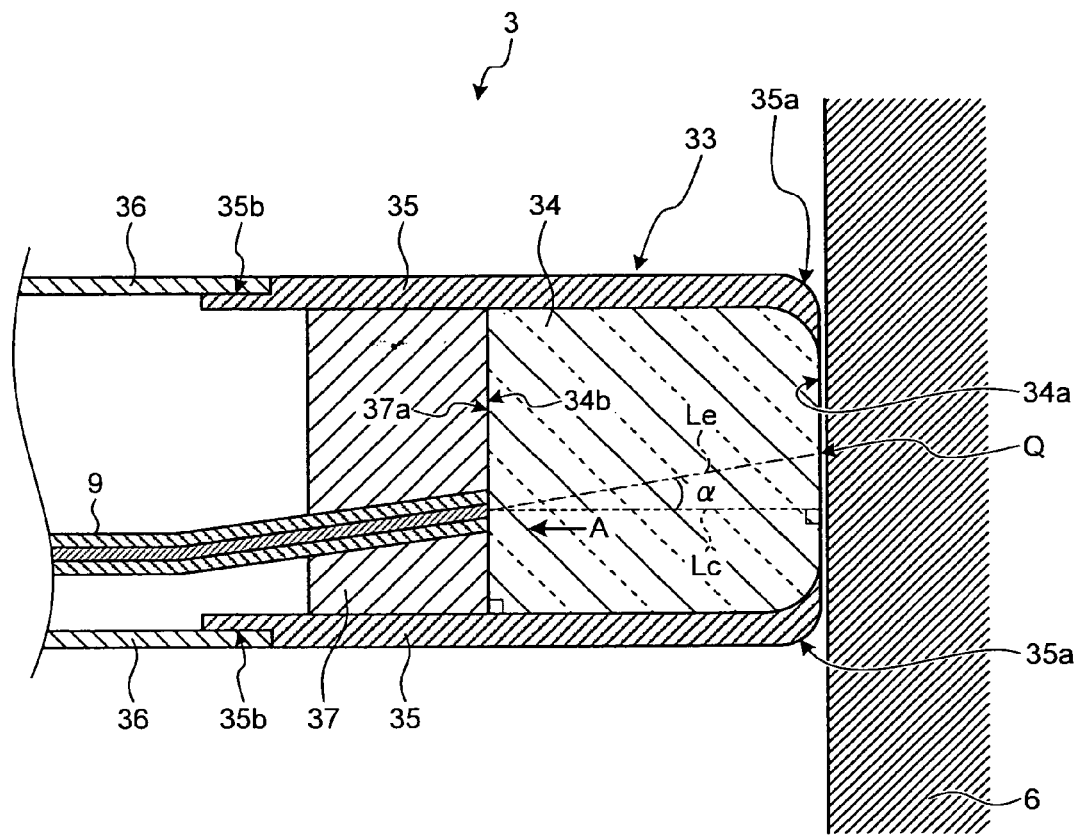
FIG. 3 is a cross-sectional view illustrating a leading end portion of the probe of FIG. 1 by cutting away along a central axis of the longitudinal direction of the probe.
Figure 4:
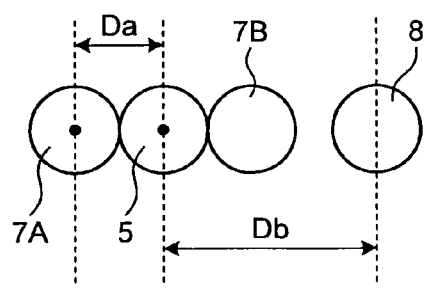
FIG. 4 is a diagram as seen from the arrow A of FIG. 3.

Next, a configuration of the leading end 33 of the probe 3 will be described in detail. FIG. 3 is a cross-sectional view illustrating the leading end portion of the probe 3 of FIG. 1 by cutting away along the central axis in the longitudinal direction of the probe. FIG. 4 is a diagram as seen from the arrow A of FIG. 3.

As illustrated in FIG. 3, a portion of the leading end 33 of the probe 3 of FIG. 1 has a configuration in which the rod 34 and the fiber unit 9 obtained by integrating the irradiation fiber 5 and the light-receiving fibers 7 and 8 are covered by a leading end casing 35 and a tube 36 fitted to the base end portion of the leading end casing 35.

The rod 34 is formed of a glass material having transparency. A leading end face 34a of the rod 34 is positioned such that it is exposed to the outside in an end portion of the leading end 33 of the probe 3 and faces the body tissue 6. The leading end face 34a of the rod 34 is perpendicular to the longitudinal direction of the probe 3. A base end face 34b of the rod 34 is formed in parallel with the leading end face 34a and is perpendicular to the longitudinal direction of the probe 3 as in the leading end face 34a. The base end face 34b of the rod 34 is arranged to abut on the leading end face of the fiber unit 9. The outer diameter of the rod 34 is substantially equal to the inner diameter of the leading end casing 35 and is fitted to the inside of the leading end casing 35. As a material of the rod 34, for example, a product S-BSL7 manufactured by OHARA Inc., may be used.

The fiber unit 9 is arranged such that the longitudinal direction of the leading end portion of the fiber unit 9 is not in parallel with the perpendicular line Lc of the leading end face 34a of the rod 34. In other words, the leading end face 34a of the rod 34 intersects with the longitudinal direction of the leading end portion of the fiber unit 9 including the plural optical fibers at an acute angle. The leading end faces of the optical fibers in the fiber unit 9 are ground such that they are in parallel with the base end face 34b and the leading end face 34a of the rod 34 and are inclined with respect to a long axis, and are arranged to abut on the base end face 34b of the rod 34. The light emitted from the fiber unit 9 is emitted to the outside from the center Q of the rod 34 through the path inclined with an angle α with respect to the perpendicular lines Lc of the leading end face 34a and the base end face 34b of the rod 34 as indicated by a path line Le. The refractive index of the rod 34 and refractive indices of the cores of respective fibers of the fiber unit 9 are set to be substantially equal in order not to make the light incident to or emergent from the fiber unit 9 refract in a boundary between the leading end face of the fiber unit 9 and the rod 34.

The irradiation fiber 5 and the light-receiving fibers 7 and 8 of the fiber unit 9 are arranged such that the distances between the leading end face 34a of the rod 34 and the irradiation fiber 5 and the light-receiving fibers 7 and 8 substantially become constant regardless of the inclination arrangement, with respect to the rod 34, of the fiber unit 9. Specifically, as the leading end face of the fiber unit 9 is seen from the light emission direction from the fiber unit 9, that is, the extending direction of the path line Le, as illustrated in FIG. 4, the irradiation fiber 5 and the light-receiving fibers 7 and 8 are arranged along a horizontal line such that the centers of the respective fibers are located on the same line. The light-receiving fibers 7A and 7B are arranged in the vicinity of the irradiation fiber 5 in the left and right sides of the irradiation fiber 5, and the light-receiving fiber 8 is further arranged on the right side of the light-receiving fiber 7B. The light-receiving fibers 7A and 7B are provided to receive the scattering light having a scattering angle of nearly 0°, and the center of the irradiation fiber 5 and each center of each light-receiving fiber 7A and 7B are separated by a distance Da. In addition, the light-receiving fiber 8 is provided to receive scattering light having a scattering angle sufficiently greater than 0°, and the center of the irradiation fiber 5 and each center of each light-receiving fiber 8 is separated by a distance Db (>Da).

Incidentally, an angle α as the inclination angle of the leading end face of the fiber unit 9 with respect to the perpendicular line Lc of the leading end face 34a is determined based on the numerical apertures NA of the irradiation fiber 5 and the light-receiving fibers 7 and 8 and refractive index of the rod 34 such that light emitted from the irradiation fiber 5 and reflected at the leading end face 34a of the rod 34 is not directly incident to the light-receiving fibers 7 and 8. In order to prevent the light, which is emitted in a direction inclined from the irradiation fiber 5 at an angle α with respect to the perpendicular line Lc and reflected on the leading end face 34a of the rod 34, from being directly incident to the light-receiving fibers 7 and 8, the light emitted from the irradiation fiber 5 may be set not to be incident to the leading end face 34a of the rod 34 perpendicularly. That is, the angle α may be set to be greater than a spread angle of the emitted light inside the rod 34 (corresponding to the numerical aperture of the fiber inside the rod 34). If the spread angle when the light from the fiber having a numerical aperture NA is incident to the rod 34 of the refractive index n is set to θ, a relationship between the numerical aperture NA, the refractive index n, and the angle θ is set as follows:

$$NA/n = \sin\theta$$

Therefore, a relationship between the angle α, the numerical aperture NA, and the refractive index n may be set as follows:

$$NA/n < \sin\alpha \qquad (1)$$

The leading end casing 35 is formed of a rigid material so that the leading end 33 of the probe 3 is not deformed by the pressing of the probe 3 to the body tissue 6. A leading end corner portion 35a of the leading end casing 35 is R-chamfered such that the body tissue 6 is not damaged when the leading end 33 of the probe 3 is pressed to the body tissue 6. In addition, the leading end corner portion 35a of the leading end casing 35 may be C-chamfered. The base end of the leading end casing 35 is provided with a notch such that its outer diameter is smaller than that of the main body of the leading end casing 35 as an engagement portion 35b that is fitted to the inner surface of the tube 36. The rod 34 is positioned such that a slippage from the leading end 33 of the probe 3 is prevented by a claw of the leading end of the inner surface of the leading end casing 35, and the leading end face 34a is appropriately located in the leading end 33 of the probe 3.

The tube 36 is formed of a soft material and extends to the base end 32 of the probe 3. The leading end of the tube 36 is engaged with the leading end casing 35 by pressedly fitted on the engagement portion 35b at the base end of the leading end casing 35 and then bonding the side face of the engagement portion 35b and the inner wall of the leading end of the tube 36 using an adhesive and the like. The outer diameter of the tube 36 is substantially equal to the outer diameter of the leading end casing 35, and a surface of the engagement portion between the leading end casing 35 and the tube 36 is stretched smoothly without any step.

A securing frame 37 is formed of a black-colored light-blocking material. Both a leading end face 37a and a base end face of the securing frame 37 are in parallel with the leading end face 34a of the rod 34. The securing frame 37 has a through-hole for inserting the fiber unit in order to allow the leading end face of the fiber unit 9 to abut on the base end face 34b of the rod 34 at an angle α. The positioning of the leading end face of the fiber unit 9 in the base end face 34b of the rod 34 is performed by arranging the securing frame 37 such that the leading end face 37a abuts on the base end face 34b of the rod 34 while the fiber unit 9 is inserted into the through-hole of the securing frame 37. The outer diameter of the securing frame 37 is substantially equal to the inner diameter of the leading end casing 35, and the securing frame 37 is fitted to the inside of the leading end casing 35.

If the scattering angle of the scattering light received by the light-receiving fibers 7A and 7B are set to 0.45°±0.22°, and the scattering angle of the scattering light received by the light-receiving fiber 8 is set to 1.20°±0.22°, the angle α as the inclination angle of the leading end surface of the fiber unit 9 is set depending on the numerical apertures NA of each fiber as indicated in Table T1.

TABLE 1

| | | Fibers | | Distance between centers of fibers | | Glass plate | | Fiber inclination α |
|---|---|---|---|---|---|---|---|---|
| | NA | Core diameter [μm] | Cladding diameter [μm] | Da [μm] | Db [μm] | Thickness T [mm] | Outer diameter φ [mm] | |
| Specification A | 0.22 | 25 | 28 | 28 to 30 | 66 | 4.8 | 2.2 | 10° |
| Specification B | 0.12 | 50 | 56 | 56 to 60 | 130 | 9.6 | 2.4 | 6.5° |

In Table T1, the angle α when the refractive index n of the glass plate of the rod 34 is set to 1.5 is provided. The angle α of Table T1 is set to be greater than the value of the angle α obtained using the formula (1). As indicated in this Table T1, in the case of specification A in which the numerical aperture NA of each fiber is set to 0.22, the angle α as the inclination angle of the fiber unit 9 is set to 10°. In addition, in the case of specification B in which the numerical aperture NA of each fiber having an increased SN by increasing the fiber diameter to be greater than that of specification A is set to 0.12, the angle α of the fiber unit 9 is set to 6.5°. Incidentally, the core diameters and the cladding diameters of each fiber, a distance Da between the center of the irradiation fiber 5 and the center of each light-receiving fiber 7A and 7B, a distance Db between the center of the irradiation fiber 5 and the center of each light-receiving fiber 8, a thickness T of the glass plate of the rod 34, an outer diameter φ of the glass plate of the rod 34 are set as indicated in specifications A and B of Table T1. Since the thickness T of the glass plate of the rod 34 is set according to a design, the outer diameter φ of the rod 34 is set based on the thickness T in order to prevent the light emitted from the irradiation fiber 5 from arriving at the side face of the glass plate.

Figure 5:
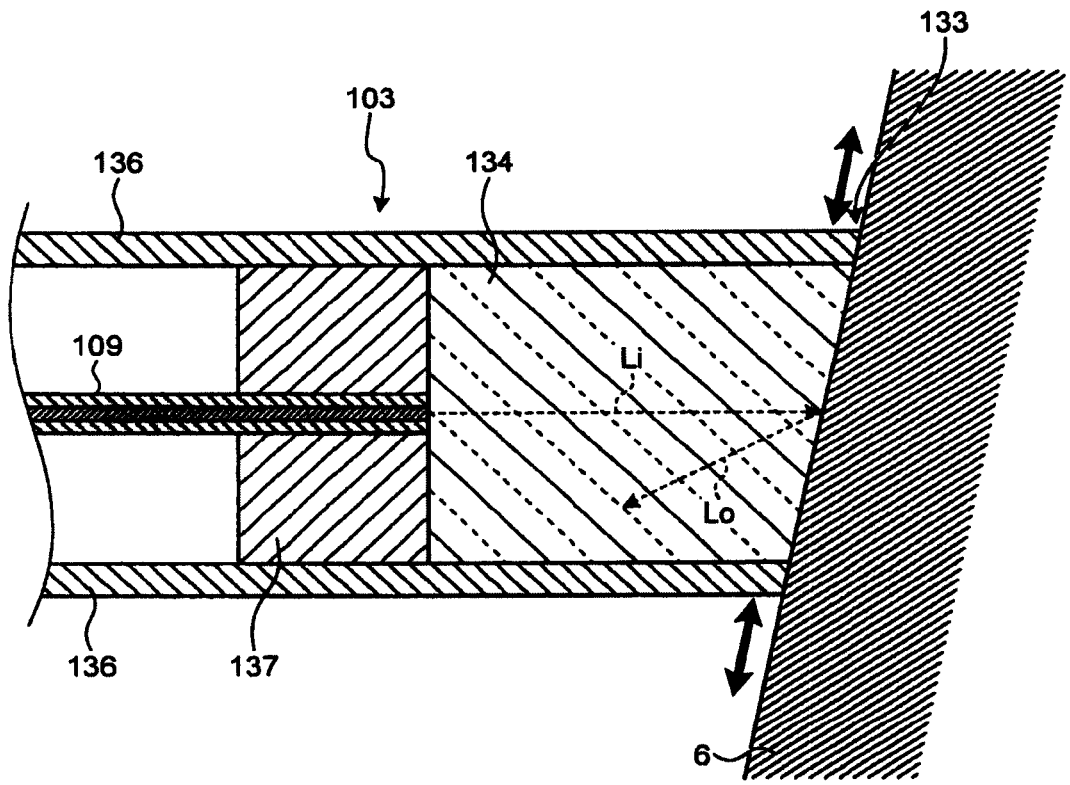
FIG. 5 is a cross-sectional view illustrating a leading end portion of the probe of the related art by cutting away along a central axis of the longitudinal direction of the probe.

In the related art, the leading end face of a rod 134 is notched with an inclination in order to prevent the light Li output from the irradiation fiber of a fiber unit 109 and undesired light Lo reflected at the leading end face of the rod 134 from arriving at the light-receiving fiber as illustrated in a probe 103 of FIG. 5. In addition, the fiber unit 109 is positioned such that the base end face of the rod 134 abuts on a securing frame 137 inside a coat material 136. In the case of the related art, since the leading end face of the rod 134 is inclined, a leading end 133 of the probe 103 may be slipped on the surface of the body tissue 6 as indicated by the arrow when the leading end 133 of the probe 103 is pressed to the body tissue 6, so that it is difficult to stabilize the position of the probe 103.

In comparison, according to the first embodiment, since the leading end face 34a of the rod 34 is perpendicular to the longitudinal direction of the probe 3, there is no slippage when the leading end of the probe 3 is pressed to the body tissue 6, and the probe 3 can make stable contact with the body tissue 6 even during the measurement.

In addition, according to the first embodiment, the fiber unit 9 is arranged such that the longitudinal direction of the leading end portion of the fiber unit 9 is not in parallel with the perpendicular line Lc of the leading end face 34a of the rod 34. In addition, the angle α as the incidence angle of the leading end face of the fiber unit 9 is determined based on the numerical apertures NA of the irradiation fiber 5 and the light-receiving fibers 7 and 8 and the refractive index of the rod 34 such that the light emitted from the irradiation fiber 5 and reflected by the leading end face 34a of the rod 34 is not directly incident to the light-receiving fibers 7 and 8. Therefore, in the probe 3 according to the first embodiment, the undesired light just reflected by the leading end face 34a of the rod 34 out of the light emitted from the irradiation fiber 5 is not overlapped on the measurement value. Therefore, it is possible to accurately obtain only the scattering light corresponding to properties of the body tissue 6 and increase the measurement accuracy.

In addition, according to the first embodiment, it is possible to increase position accuracy between the leading ends of fibers and improve mountability of the fiber unit 9 into the probe 3 by integrating each fiber into the fiber unit 9. In addition, by grinding the leading end face of each fiber while each fiber is integrated into the fiber unit 9, there is no need to perform a grinding process of the fiber end face for each fiber, and it is possible to simplify the grinding process of the fiber end face and facilitate bonding of the rod 34 to the base end face 34b of the fiber unit 9. Furthermore, since the securing frame 37 is formed of a light-blocking material, it is also possible to prevent the light leaking from the side face of the irradiation fiber 5 from being incident to the light-receiving fibers 7 and 8.

Furthermore., according to the first embodiment, since the leading end corner portion 35a of the leading end casing 35 in the leading end of the probe 3 is chamfered, it is possible to reduce a possibility of damage to the body tissue 6 in the channel side wall of the endoscope where the probe 3 is inserted.

Figure 6:
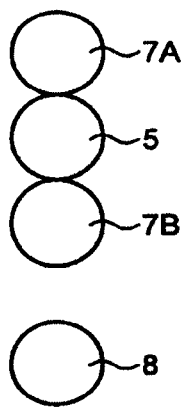
FIG. 6 is another diagram as seen from the arrow A of FIG. 3.
Figure 7:
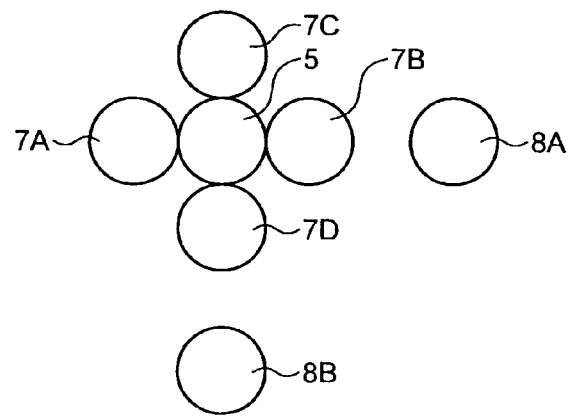
FIG. 7 is still another diagram as seen from the arrow A of FIG. 3.

The irradiation fiber 5 and the light-receiving fibers 7 and 8 of the fiber unit 9 are not limited to the arrangement of FIG. 4. For example, as illustrated in FIG. 6, the irradiation fiber 5 and the light-receiving fibers 7A, 7B, and 8 may be arranged along a vertical line such that the centers of respective fiber are located on the same line as the leading end face of the fiber unit 9 is seen from the extending direction of the path line Le. As illustrated in FIG. 7, compared to the configuration of FIG. 4, the light-receiving fibers 7C and 7D may be arranged over and under the irradiation fiber 5, and the light-receiving fiber 8B may be arranged under the light-receiving fiber 7D along with the light-receiving fiber 8A, so that the received light amount of the scattering light of each scattering angle can be obtained cumulatively.

Second Embodiment

Next, a second embodiment will be described. In the second embodiment, description will be made for a case where not the leading end face of each fiber but the base end face of the rod is not in parallel with the leading end face of the rod.

Figure 8:
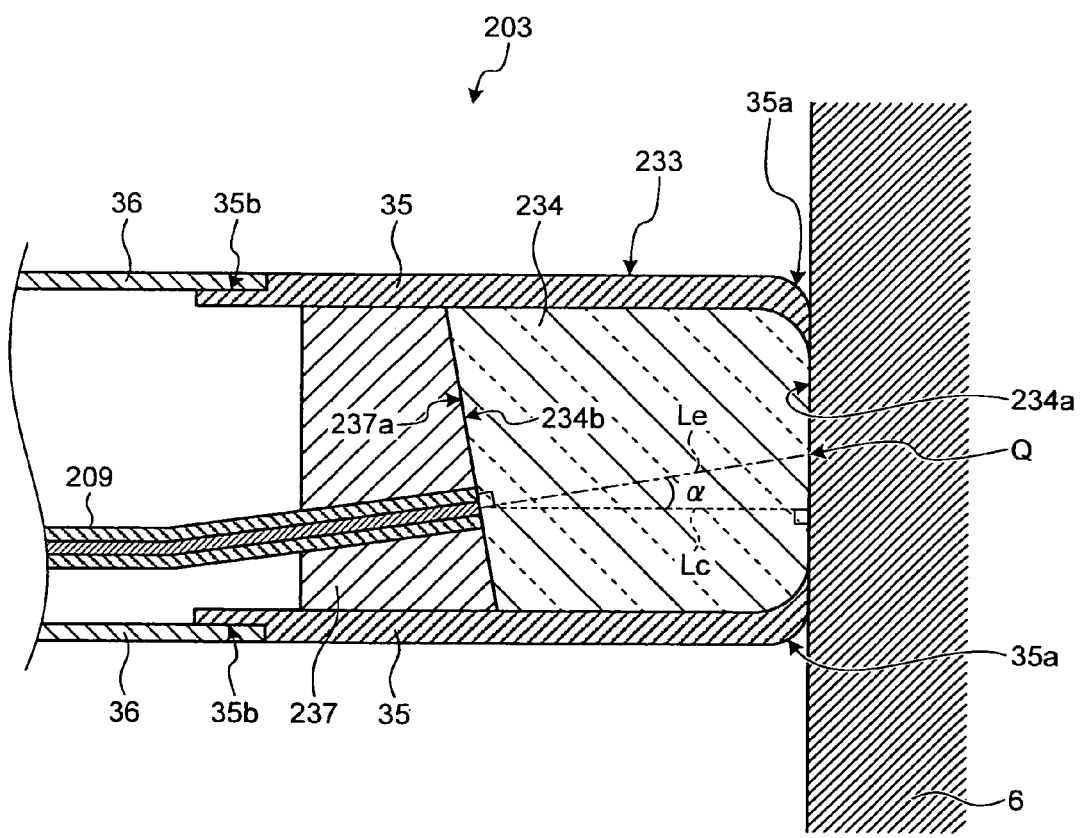
FIG. 8 is a cross-sectional view illustrating a leading end portion of a probe according to the second embodiment by cutting away along the central axis of the longitudinal direction of the probe.

FIG. 8 is a cross-sectional view illustrating a leading end portion of a probe according to the second embodiment by cutting away along the central axis of the longitudinal direction of the probe. As illustrated in FIG. 8, in a portion of a leading end 233 of a probe 203 according to the second embodiment has a configuration in which a fiber unit 209 obtained by integrating the irradiation fiber 5 and the light-receiving fibers 7 and 8 and a rod 234 are covered by the leading end casing 35 and the tube 36.

The rod 234 is formed of the same material as that of the rod 34 of the first embodiment, and is positioned such that a leading end face 234a is located in the end portion of the leading end 233 of the probe 203. Similar to the rod 34, the leading end face 234a of the rod 234 is perpendicular to the longitudinal direction of the probe 203. In comparison, a base end face 234b of the rod 234 is formed to be not in parallel with the leading end face 234a.

The fiber unit 209 is arranged to abut on the base end face 234b of the rod 234 by grinding each leading end face of optical fibers in the fiber unit 209 to be perpendicular to a long axis in parallel with the base end face 234b of the rod 234. In this case, since the base end face 234b of the rod 234 is not in parallel with the leading end face 234a, similar to the first embodiment, the longitudinal direction of the leading end portion of the fiber unit 209 is arranged not to be in parallel with the perpendicular line Lc of the leading end face 234a of the rod 234. The light emitted from the fiber unit 209 passes through the path inclined at an angle α with respect to the perpendicular line Lc of the leading end face 234a of the rod 234 and is emitted to the outer side from the center Q of the rod 234 as illustrated in the line Le. Incidentally, the irradiation fiber 5 and the light-receiving fibers 7 and 8 of the fiber unit 209 are arranged in any one of the configurations illustrated in FIG. 4, 6, or 7 described in conjunction with the first embodiment.

Similarly, in this case, the angle α which is the inclination angle of the leading end face of the fiber unit 209 with respect to the perpendicular line Lc of the leading end face 234a is determined depending on the numerical apertures NA of the irradiation fiber 5 and the light-receiving fibers 7 and 8 and the refractive index of the rod 234 based on the relationship of the formula (1) described above in the first embodiment so as to prevent the light just reflected by the leading end face 234a of the rod 234 out of the light emitted from the irradiation fiber 5 from being directly incident to the light-receiving fibers 7 and 8. For example, similar to the first embodiment, if the scattering angle of the scattering light received by the light-receiving fiber 7 is set to 0.45°±0.22°, and the scattering angle of the scattering light received by the light-receiving fiber 8 is set to 1.20°±0.22°, and if the numerical aperture NA of each fiber is set to 0.22, the inclination α of the fiber unit 209 is set to 10° as indicated in specification A of Table T1. In this case, the core diameter and the cladding diameter of each fiber, the distances Da and Db, the thickness T of the glass plate of the rod 234, and the outer diameter φ of the glass plate are set to be equal to those of specification A of Table T1.

A securing frame 237 is formed of a black-colored light-blocking material. A leading end face 237a of the securing frame 237 is in parallel with the base end face 234b of the rod 234. The securing frame 237 is internally provided with a through-hole for inserting the fiber unit in order to allow the leading end face of the fiber unit 209 to perpendicularly abut on the base end face 234b. Positioning of the leading end face of the fiber unit 209 relative to the base end face 234b of the rod 234 is performed by arranging the securing frame 237 such that the leading end face 237a abuts on the base end face 234b of the rod 234 while the fiber unit 209 is inserted into the through-hole of the securing frame 237. Positioning markers are added to each of the outer face of the securing frame 237 and the outer face of the rod 234 in order to prevent the securing frame 237 from rotating around the axis.

Even when not the leading end face of each fiber but the base end face of the rod is not in parallel with the leading end face of the rod, and respective leading end faces of optical fibers are in parallel with the base end face 234b of the rod 234 as in the second embodiment, it is possible to prevent a slippage when the leading end of the probe 203 is pressed to the body tissue 6, and undesired light emitted from the irradiation fiber 5 and reflected by the leading end face 234a of the rod 234 is not overlapped on the measurement value. In addition, since the leading end face of the fiber unit 209 is ground to be perpendicular to a long axis, it is possible to simplify a grinding process of the leading end face of the fiber unit 209.

Third Embodiment

Next, a third embodiment will be described. In the third embodiment, a configuration of the connector 23 of the main unit 2 and a configuration of the connector portion in the base end side of the probe will be described.

Figure 9:
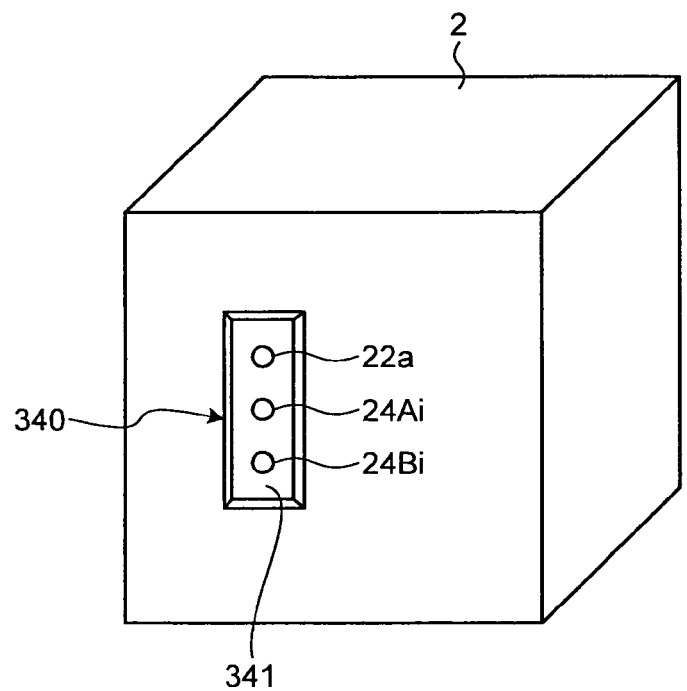
FIG. 9 is a perspective view illustrating a main unit as seen from a connector face.
Figure 10:
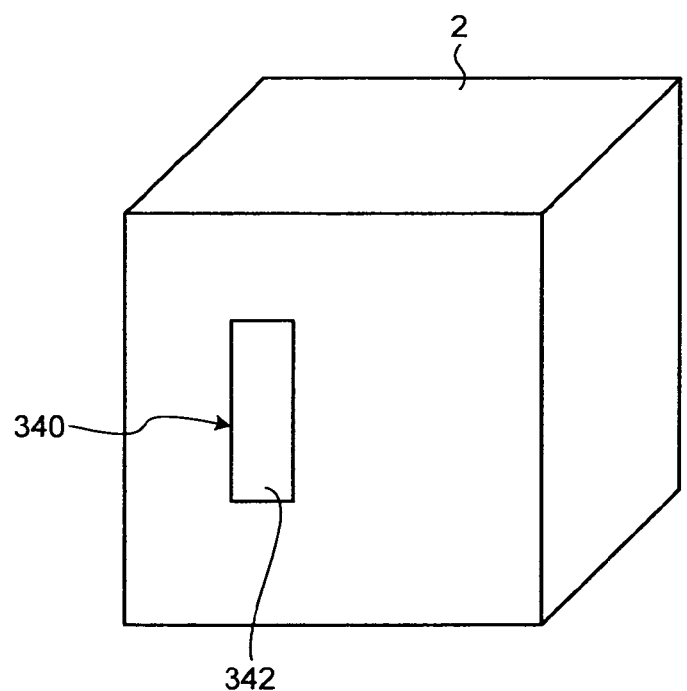
FIG. 10 is a perspective view illustrating the main unit as seen from a connector face.

FIGS. 9 and 10 are perspective views as seen from the connector 23 face of the main unit 2. As illustrated in FIG. 9, a connector forming portion 340 is provided with a rectangular hollow portion 341 where a connector portion of the base end of the probe 3 is introduced. The bottom face of the hollow portion 341 is provided with a light emission face 22a from the LED of the light source unit 22 and a light incidence face 24Ai and 24Bi to the spectroscope of the measurement unit 24. For example, the light incidence face 24Ai receives the light output from the base end of the light-receiving fiber 7 of the probe 3 and the light incidence face 24Bi receives the light output from the base end of the light-receiving fiber 8 of the probe 3.

As illustrated in FIG. 10, the opening of the hollow portion 341 is covered by the door 342 when the probe 3 is not connected. Thus, it is possible to avoid dust or contamination from intruding into the hollow portion 341, prevent dust or contamination from being adhered to the light emission face 22a and the light incidence faces 24Ai and 24Bi, prevent a malfunction of the apparatus, and ensure accurate measurement.

Figure 11:
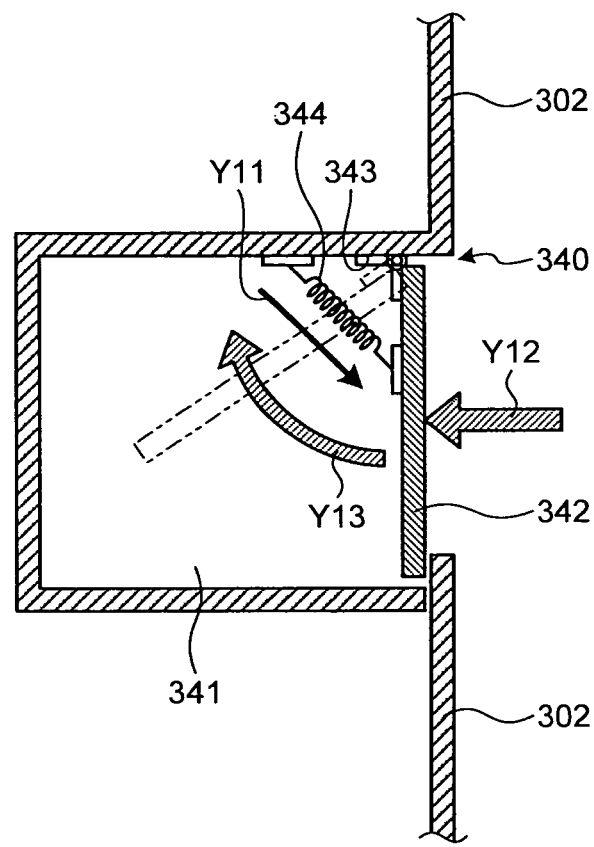
FIG. 11 is a horizontal cutaway view illustrating a connector forming portion of the main unit.

FIG. 11 is a horizontal cutaway view illustrating the connector forming portion 340 of the main unit 2. The hollow portion 341 of the main unit 2 is formed in a casing 302 of the main unit, and the opening of the hollow portion 341 is covered by the openable door 342. One end of the door 342 is attached to the side face in the vicinity of the opening of the hollow portion 341 using a hinge 343. The door 342 is not opened as long as an external force is not applied since a biasing force is applied from the side face of the hollow portion 341 to the opening using a spring 344 attached to the side face of the hollow portion 341 as indicated by the arrow Y11. The spring 344 is contracted, and the door 342 is opened as indicated by the arrow Y13 when the door 342 is pressed by the connector portion of the base end of the probe 3 from an outer side as indicated by the arrow Y12.

Figure 12:
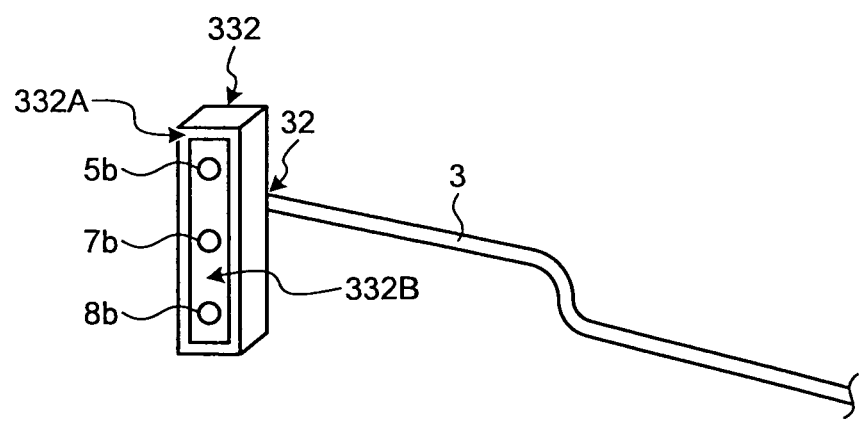
FIG. 12 is a perspective view illustrating a connector portion of a probe base end.
Figure 13:
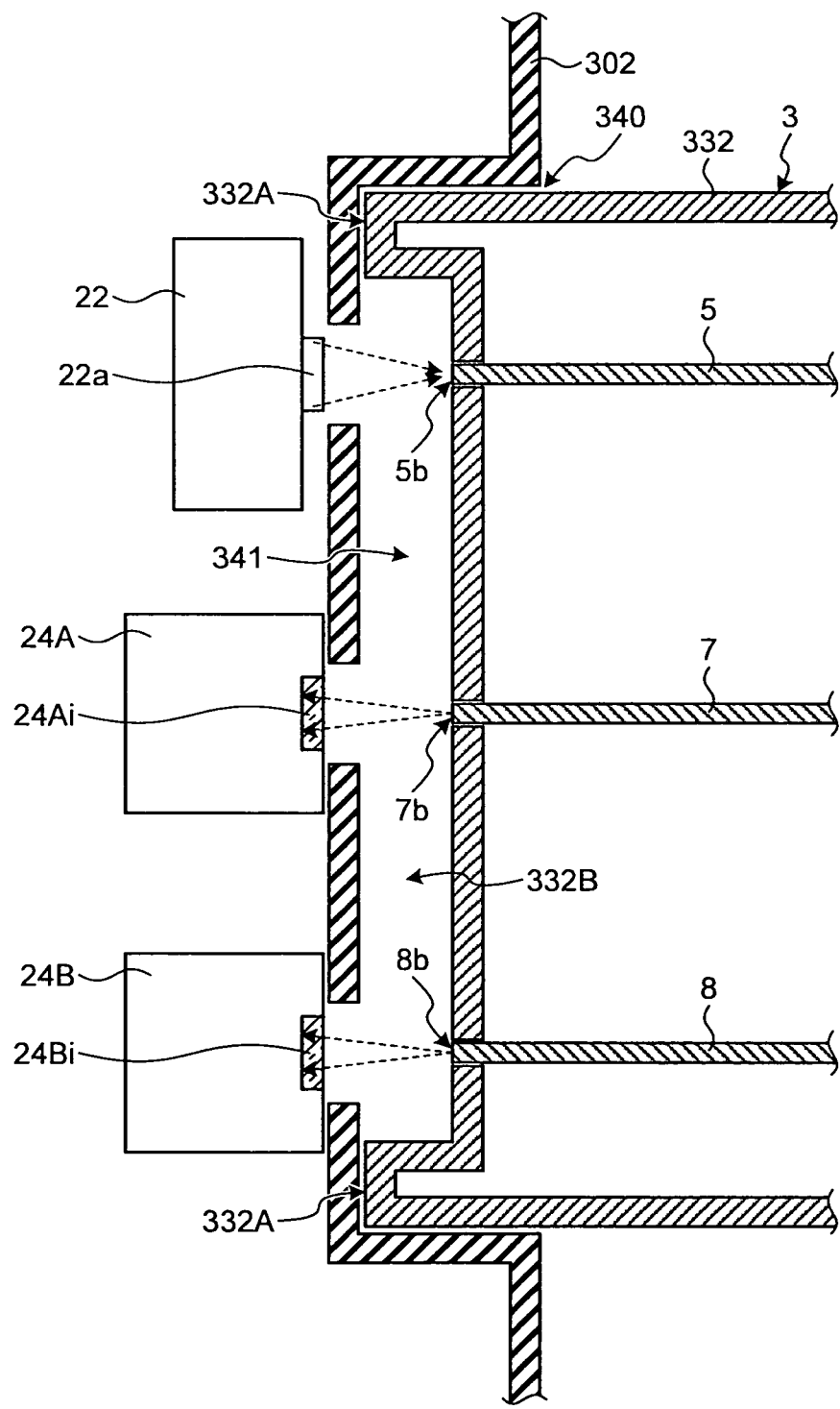
FIG. 13 is a vertical cutaway view illustrating a connector forming portion of the main unit of FIG. 10 when the probe of FIG. 12 is connected.
Figure 14:
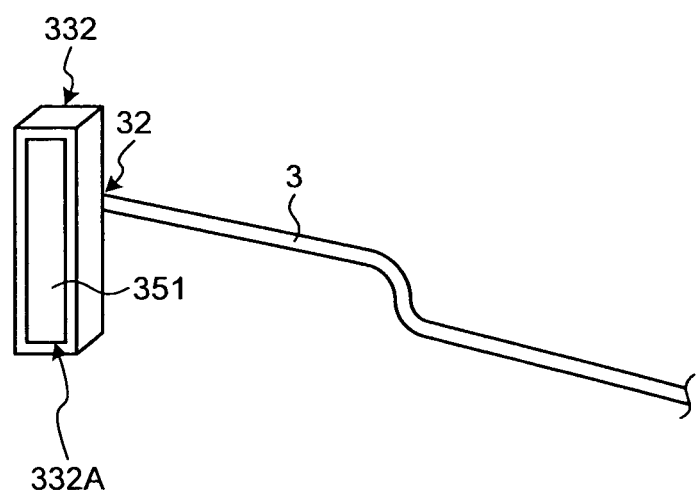
FIG. 14 is a perspective view illustrating a connector portion of a probe base end before use.

Next, the connector portion of the base end of the probe 3 will be described with reference to FIGS. 12 to 14. FIG. 12 is a perspective view illustrating the connector portion of the base end of the probe 3. FIG. 13 is a vertical cutaway view illustrating the connector forming portion 340 of the main unit 2 when the probe is connected. FIG. 14 is a perspective view illustrating the connector portion of the base end of the probe 3 before use.

As illustrated in FIGS. 12 and 13, in a connector portion 332 provided in the base end 32 of the probe 3, an end face 332A is provided with a hollow portion 332B, and a bottom face of the hollow portion 332B is provided with respective end faces of a base end 5b of the irradiation fiber 5 of the light source unit 22, a base end 7b of the light-receiving fiber 7, and the base end 8b of the light-receiving fiber 8. The arrangement on the bottom face of the hollow portion 332B is made such that the end face of the base end 5b of the irradiation fiber 5 faces the light emission face 22a of the main unit 2, the end face of the base end 7b of the light-receiving fiber 7 faces the light incidence face 24Ai of the spectroscope 24A of the measurement unit 24, the end face of the base end 8b of the light-receiving fiber 8 faces the light incidence face 24Bi of the spectroscope 24B of the measurement unit 24 when the probe 3 is connected to the main unit 2. Since the end faces of each fiber are provided on the bottom face of the hollow portion 332B of the connector portion 332, the light emission face 22a and the light incidence faces 24Ai and 24Bi of the casing 302 of the main unit 2 do not make contact with the end face of the irradiation fiber 5 of the probe 3 and the end faces of the light-receiving fibers 7 and 8 when the probe 3 is connected to the main unit 2, so that it is possible to avoid a breakdown of the end face of the fiber.

The probe 3 may be replaced with a new probe in every single examination. Since the core diameter of each fiber is set to approximately 50 μm, accurate measurement is hindered even when a small size of dust or contamination is adhered. For this reason, adherence of dust or contamination to the end face of each fiber is prevented if the probe 3 is shipped from a factory by attaching a seal 351 to the end face 332A of the connector portion 332, and an operator removes the seal 351 before optical measurement and then connects the connector portion 332 of the probe 3 to the main unit 2.

In the main unit 2, the diameter of the light emission face 22a of the light source unit 22 is smaller than the diameter of the light-receiving area on the end face of the base end 5b of the irradiation fiber 5 of the connector portion 332 of the probe 3. For this reason, there is no loss in the light amount even when the base end 5b of the irradiation fiber 5 is decentered, so that it is not necessary to increase the accuracy for preventing decentering of the base end 5b of the irradiation fiber 5.

In addition, the diameters of the light-emitting area on the end faces of the light-receiving fibers 7 and 8 are smaller than the diameters of the light incidence faces 24Ai and 24Bi of the measurement unit 24. For this reason, there is no loss in the light amount even when the base ends 7b and 8b of the light-receiving fibers 7 and 8 are decentered, and it is not necessary to increase accuracy for preventing decentering of the base ends 7b and 8b of the light-receiving fibers 7 and 8.

When the probe 3 is connected to the main unit 2, the light emission face 22a and the light incidence faces 24Ai and 24Bi of the casing 302 of the main unit 2 do not make contact with the end face of the irradiation fiber 5 and the end face of light-receiving fibers 7 and 8 of the probe 3. The diameter of the light emission face 22a of the light source unit 22 is smaller than the diameter of the light-receiving area of the end face of the base end 5b of the irradiation fiber 5 of the connector portion 332 of the probe 3. The diameters of the light incidence faces 24Ai and 24Bi of the measurement unit 24 are smaller than the diameters of the light-emitting areas of the end faces of the light-receiving fibers 7 and 8. For these purposes, it is necessary to satisfy the following formulas (2) to (5).

$$\phi1 > \phi2 + 2 \times D1 \times \tan(\theta1) \quad (2)$$

$$D1 > 0.1 \text{ mm} \quad (3)$$

$$\phi3 > \phi4 + 2 \times D2 \times \tan(\theta2) \quad (4)$$

$$D2 > 0.1 \text{ mm} \quad (5)$$

In the formulas (2) to (5), $\phi1$ denotes a diameter of the light emission face 22a of the light source unit 22, $\phi2$ denotes a diameter of the core of the irradiation fiber 5, and $\phi3$ denotes a diameter of the light incidence faces 24Ai and 24Bi to the spectroscopes 24A and 24B of the measurement unit 24. In addition, in the formulas (2) to (5), $\phi4$ denotes a diameter of the core of the light-receiving fibers 7 and 8, D1 denotes an air-equivalent distance between the light emission face 22a of the light source unit 22 and end face of the irradiation fiber 5, D2 denotes an air-equivalent distance between the light incidence faces 24Ai and 24Bi to the spectroscope and the end faces of the light-receiving fibers 7 and 8, θ1 denotes a light-receiving angle of the irradiation fiber 5, and θ2 denotes a light-receiving angles of the light-receiving fibers 7 and 8.

In this manner, according to the third embodiment, when the probe 3 is connected to the main unit 2, the light incidence faces 24Ai and 24Bi and the light emission face 22a of the casing 302 of the main unit 2 do not make contact with the end face of the light-receiving fibers 7 and 8 the end face of the irradiation fiber 5 of the probe 3. Therefore, it is possible to avoid a breakdown of the fiber end face. In addition, it is possible to implement optical measurement having excellent efficiency with a reduced loss in the light amount of the irradiation fiber 5 and the light-receiving fibers 7 and 8 by setting each element to satisfy the formulas (2) to (5) described above.

Fourth Embodiment

Next, a fourth embodiment will be described. According to the fourth embodiment, another example will be described regarding a configuration of the connector of the main unit and a configuration of the connector portion in the base end side of the probe.

Figure 15:
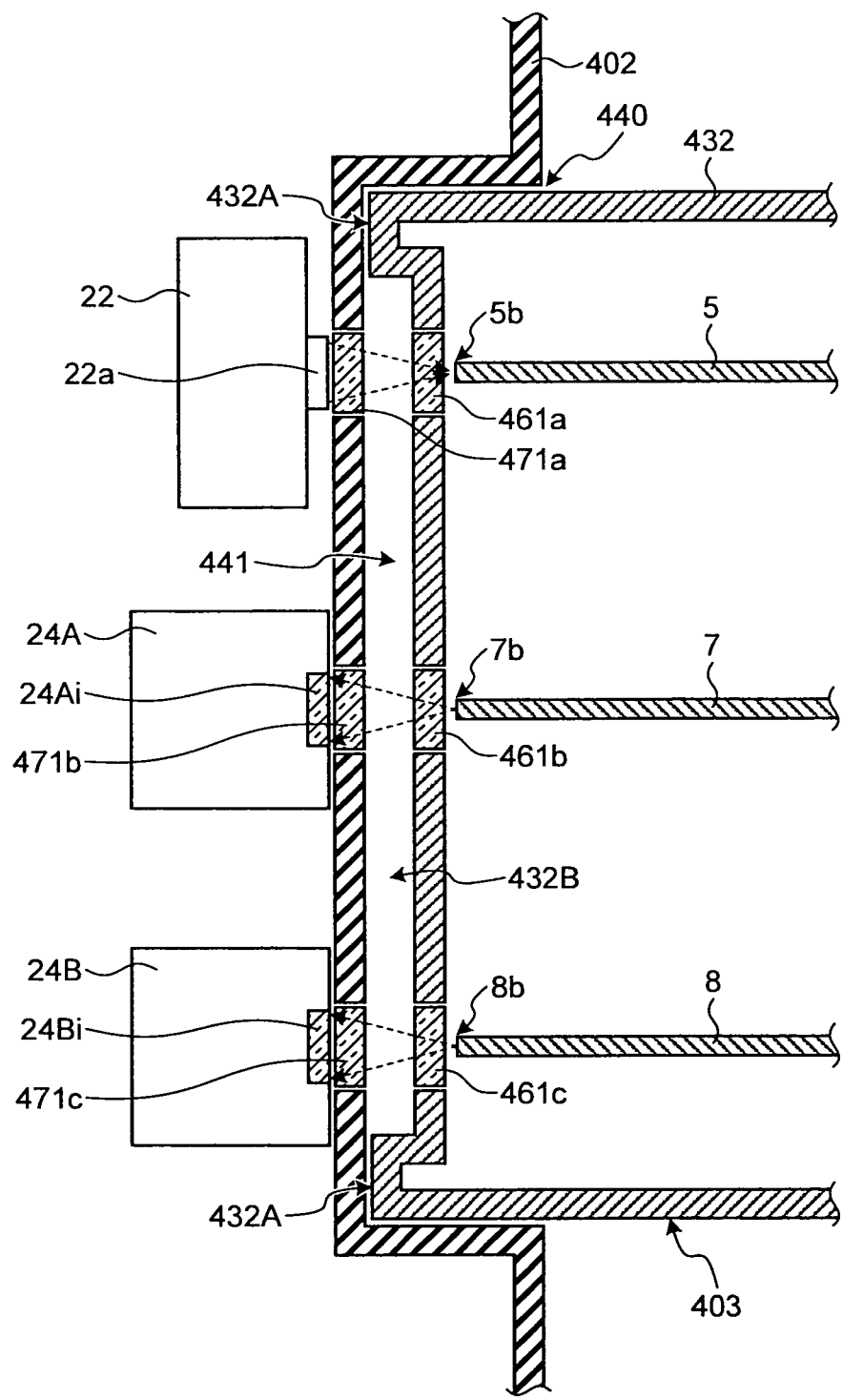
FIG. 15 is a vertical cutaway view illustrating a connector forming portion of the main unit when a probe base end according to a fourth embodiment is connected to the connector portion.

FIG. 15 is a vertical cutaway view illustrating the connector forming portion of the main unit when the probe base end is connected to the connector portion according to the fourth embodiment.

Similar to the probe 3, a connector portion 432 of the base end of a probe 403 according to the fourth embodiment is provided with a hollow portion 432B on an end face 432A as illustrated in FIG. 15. Out of the bottom face of the hollow portion 432B, respective end faces and facing areas of the base end 5b of the irradiation fiber 5 of the light source unit 22, the base end 7b of the light-receiving fiber 7, and the base end 8b of the light-receiving fiber 8 are sealed with glass plates 461a to 461c. That is, adherence of dust or contamination to the end face of each fiber is prevented by avoiding exposure of the end face of the base end of each fiber. In addition, since a certain distance is secured between each end face of the fiber and the glass plates 461a to 461c, a diameter of the area of the light emitted from the irradiation fiber 5 on the glass plate 461a side and a diameter of the area of the light incident from the light-receiving fibers 7 and 8 on the glass plates 461b side and 461c side become sufficiently larger than the diameter of the core of each fiber. Therefore, even when dust or contamination is adhered to the glass plates 461a to 461c, it is possible to significantly reduce influence of dust or contamination, compared to a case where dust or contamination is adhered to the end face of each fiber.

In addition, as illustrated in a casing 402 of FIG. 15, out of the bottom face of a hollow portion 441 of a connector forming portion 440, the area facing the light emission face 22a from the LED of the light source unit 22 and the light incidence faces 24Ai and 24Bi to the spectroscope of the measurement unit 24 is sealed with glass plates 471a to 471c. That is, it is possible to prevent adherence of dust or contamination to the light emission face 22a and the light incidence faces 24Ai and 24Bi by avoiding exposure of the light emission face 22a and the light incidence faces 24Ai and 24Bi.

In this manner, according to the fourth embodiment, it is possible to obtain advantages similar to those of the third embodiment. In addition, it is possible to improve measurement accuracy by further reducing influence of dust or contamination.

Figure 16:
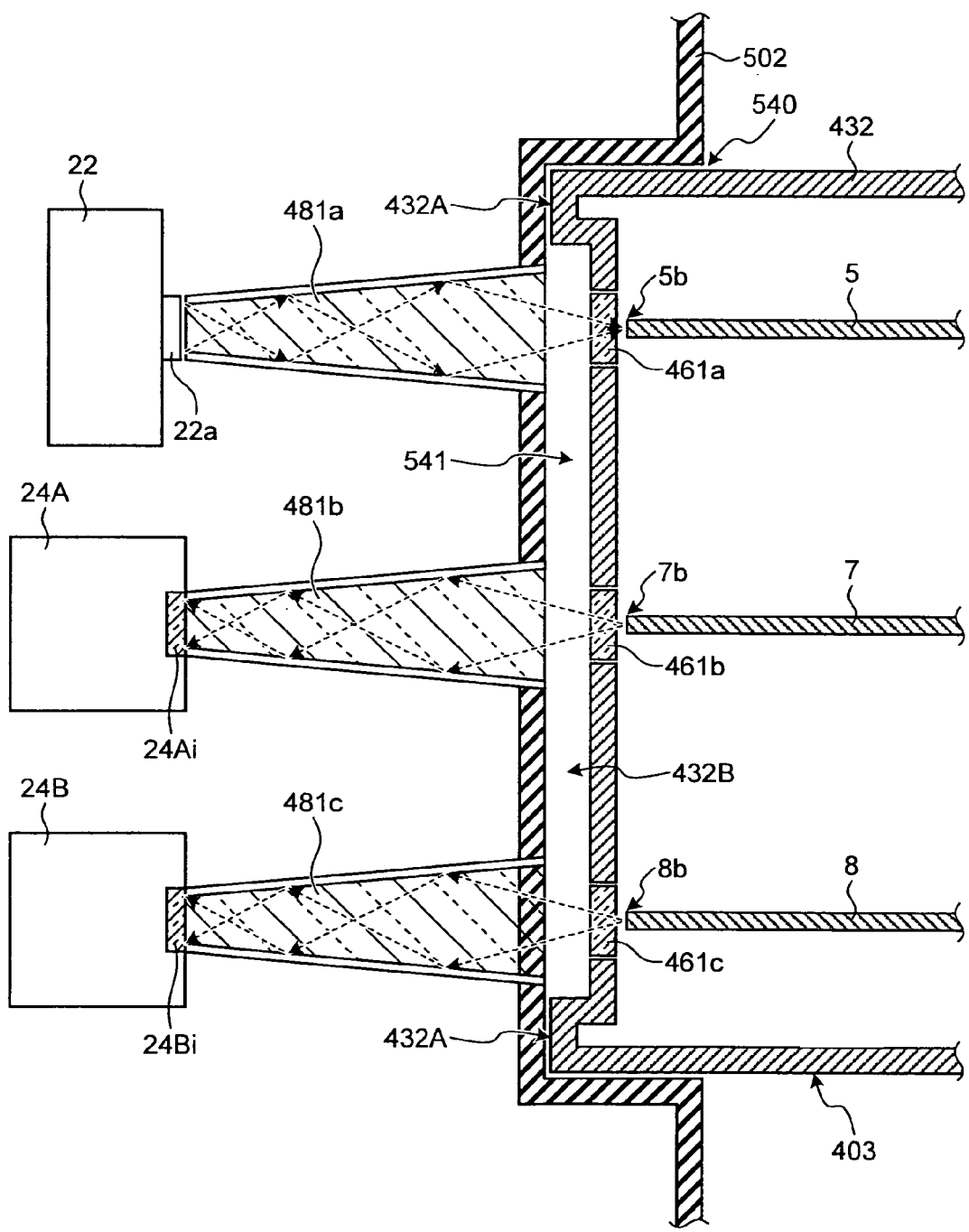
FIG. 16 is a vertical cutaway view illustrating another exemplary connector forming portion of the main unit when the probe base end is connected to the connector portion according to the fourth embodiment.

The main unit according to the fourth embodiment may have a configuration in which the bottom face of a hollow portion 541 of a connector forming portion 540 is provided optical tapered rods 481a to 481c corresponding to the light emission face 22a from the LED of the light source unit 22 and the light incidence faces 24Ai and 24Bi to the spectroscope of the measurement unit 24, respectively, as illustrated in a casing 502 of FIG. 16.

In the configuration of FIG. 16, since the light is emitted from the light emission face 22a of the light source unit 22 to the probe 403 by way of the optical tapered rod 481a, it is possible to increase a diameter of the area of the light emitted from the casing 502 in practice to be larger than the diameter of the light emission face 22a. Therefore, even when dust or contamination is adhered to the end face of the optical tapered rod 481a in the probe 403 side, it is possible to significantly reduce influence caused by dust or contamination, compared to a case where dust or contamination is adhered to the light emission face 22a. In addition, since a diameter of the area of the light emitted in practice is larger than the diameter of the light emission face 22a, it is possible to reduce a loss in the light amount without increasing accuracy for suppressing decentering of the base end 5b of the irradiation fiber 5. In addition, since the intensity distribution of the light emitted from the light source unit 22 can be equalized by the optical tapered rod 481a, it is possible to stabilize the light amount incident to the irradiation fiber 5.

In the configuration of FIG. 16, since the light is incident to the light incidence faces 24Ai and 24Bi of the spectroscope by way of the optical tapered rods 481b and 481c, it is possible to increase the diameter of the area of the light incident to the casing 502 from the light-receiving fibers 7 and 8 in practice to be larger than the diameters of the light incidence faces 24Ai and 24Bi. Even when dust or contamination is adhered to the optical tapered rods 481b and 481c, it is possible to significantly reduce, influence caused by dust or contamination, compared to a case where dust or contamination is adhered to the surfaces of each light incidence faces 24Ai and 24Bi. In addition, since the diameter of the area of the light incident in practice increases to be larger than the diameter of the light incidence faces 24Ai and 24Bi, it is possible to reduce a loss in the light amount without increasing accuracy for suppressing decentering of the base ends 7b and 8b of the light-receiving fibers 7 and 8.

In addition, as illustrated in FIG. 16, by arranging the optical tapered rods 481a to 481c in the light emission face 22a and the light incidence faces 24Ai and 24Bi, it is possible to flexibly set the positions of the LED of the light source unit 22 and each spectroscope of the measurement unit 24 in the casing 502 and miniaturize the casing 502.

Figure 17:
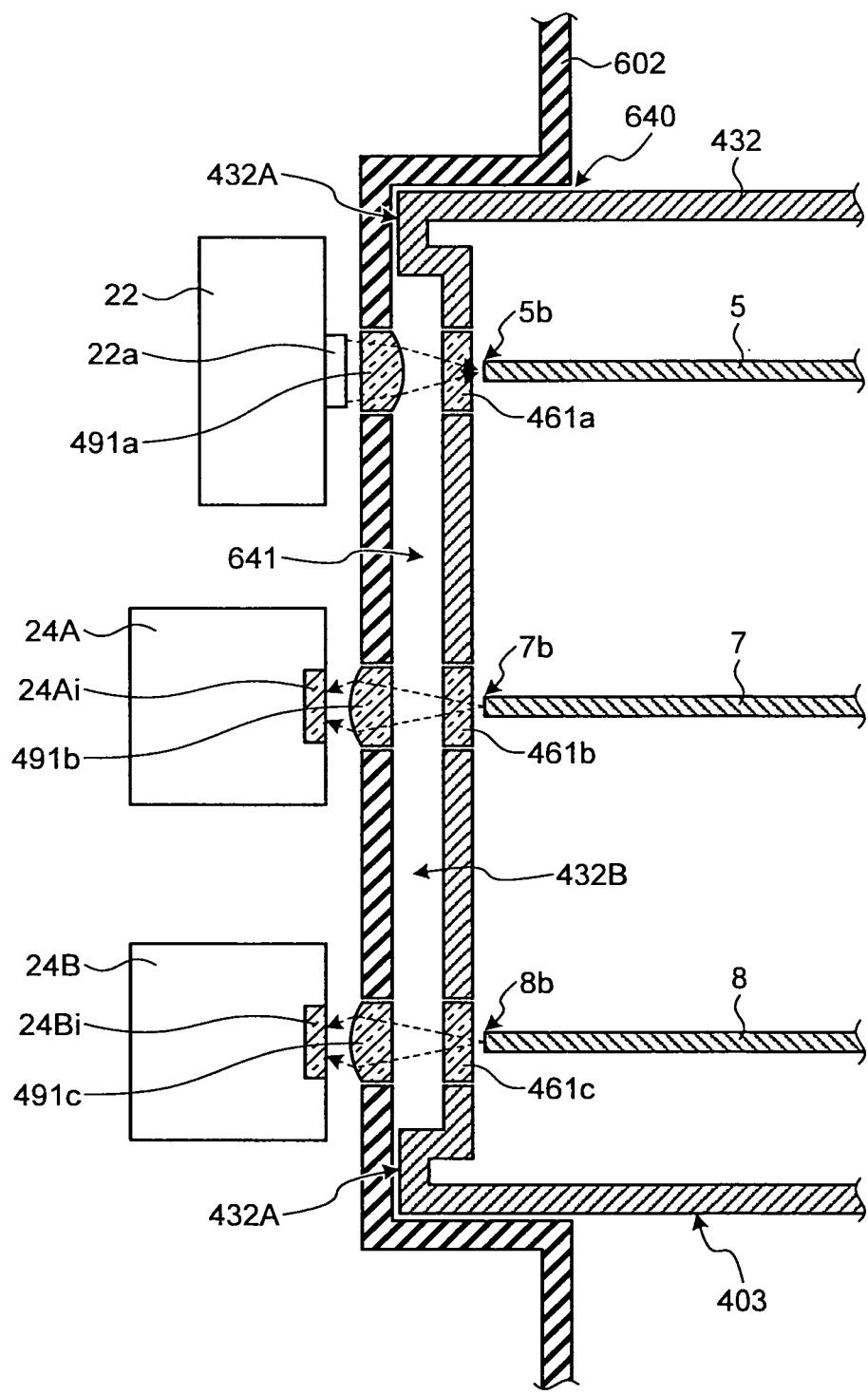
FIG. 17 is a vertical cutaway view illustrating another exemplary connector forming portion of the main unit when the probe base end according to the fourth embodiment is connected to the connector portion.

As illustrated in a casing 602 of FIG. 17, the bottom face of a hollow portion 641 of a connector forming portion 640 may be provided with lenses 491a to 491c corresponding to the light emission face 22a and the light incidence faces 24Ai and 24Bi, respectively. Similarly, in this case, it is possible to increase the diameter of the area of the light emitted from the casing 602 in practice to be larger than the diameter of the light emission face 22a, and it is possible to increase the diameter of the area of the light incident to the casing 602 from light-receiving fibers 7 and 8 in practice to be larger than the diameter of the light incidence faces 24Ai and 24Bi. For this reason, even when dust or contamination is adhered to the end face of each lens 491a to 491c in the probe 403 side, it is possible to significantly reduce influence caused by dust or contamination, compared to a case where dust or contamination is adhered to the light emission face 22a or the light incidence faces 24Ai and 24Bi. In addition, a loss in the light amount is reduced without increasing accuracy for suppressing decentering of the base end 5b of the irradiation fiber 5 and the base ends 7b and 8b of the light-receiving fibers 7 and 8. Similar to the casing 502, in the casing 602, it is also possible to flexibly set the positions of the LED of the light source unit 22 and each spectroscope of the measurement unit 24 in the casing 602.

Figure 18:
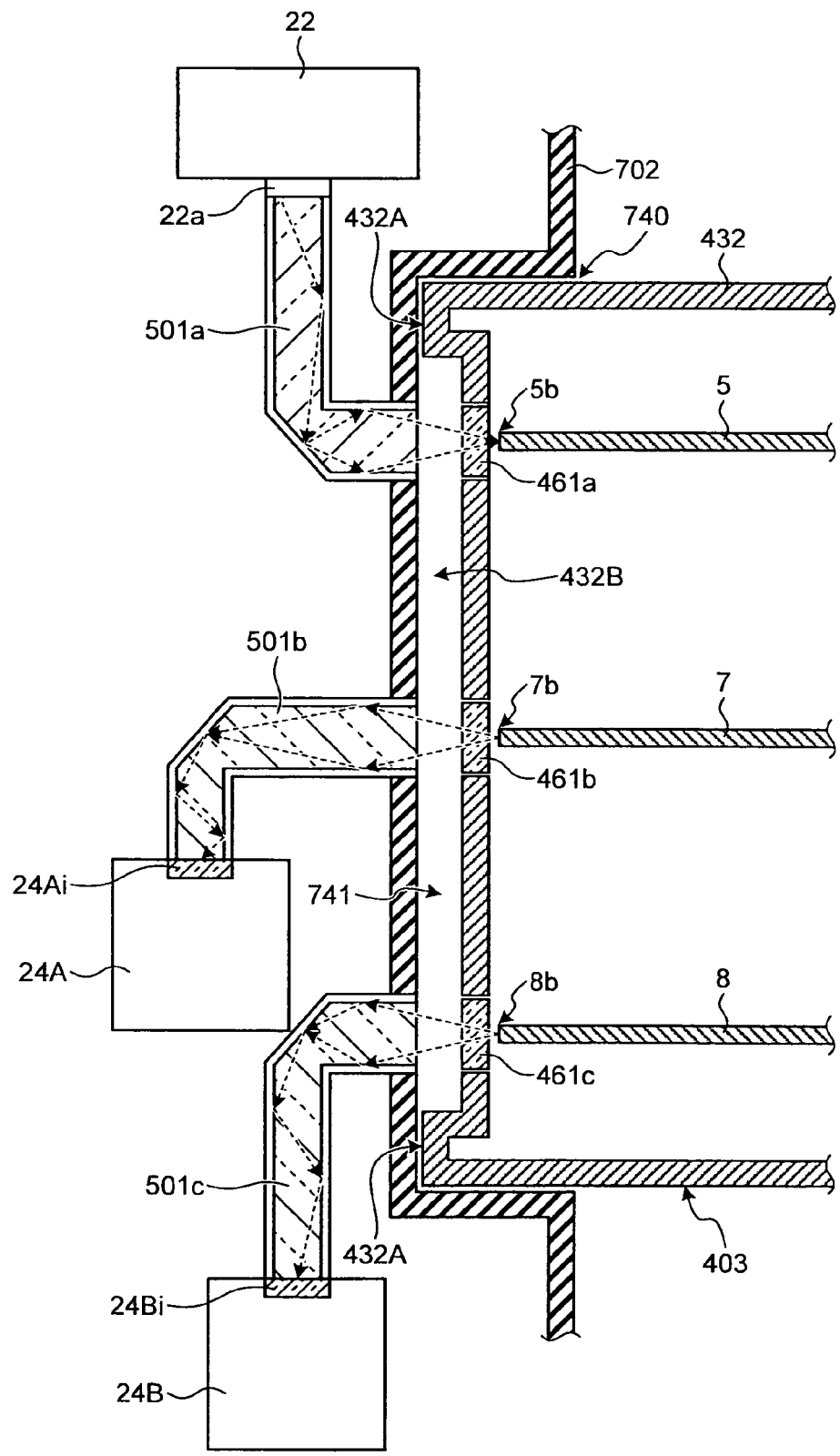
FIG. 18 is a vertical cutaway view illustrating another exemplary connector forming portion of the main unit when the probe base end according to the fourth embodiment is connected to the connector portion.

As illustrated in a casing 702 of FIG. 18, the bottom face of a hollow portion 741 of a connector forming portion 740 may be provided with squared rods 501a to 501c corresponding to the light emission face 22a and the light incidence faces 24Ai and 24Bi. In this case, it is possible to flexibly set the positions of the LED of the light source unit 22 and each spectroscope of the measurement unit 24 in the casing 702.

In the casing of the main unit, it is not necessary to provide the same optical member for both the light emission face 22a and the light incidence faces 24Ai and 24Bi. It may be possible to freely select an optical member out of the glass plate, the optical tapered rod, the lens, or the squared rod for each position of the LED of the light source unit 22 and each spectroscope of the measurement unit 24 in the casing. Similarly, according to the fourth embodiment, it is possible to reliably perform optical measurement with excellent efficiency and with a reduced loss in the light amount of the irradiation fiber 5 and the light-receiving fibers 7 and 8 by setting each element to satisfy the formulas (2) to (5) described in the third embodiment.

Fifth Embodiment

Next, a fifth embodiment will be described. According to the fifth embodiment, description will be made for another example of a configuration of the connector of the main unit and a configuration of the connector portion of the based end side of the probe.

Figure 19:
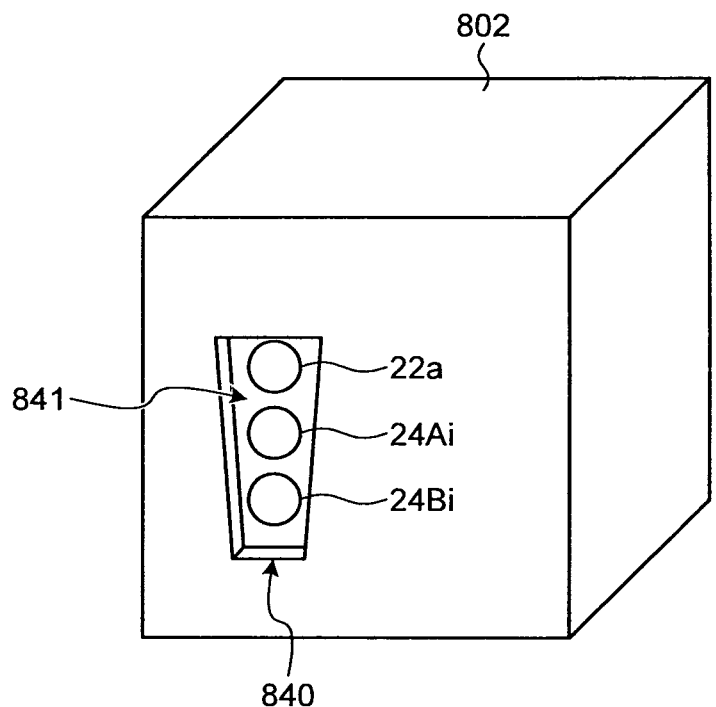
FIG. 19 is perspective view as seen from a connector face of a main unit according to the fifth embodiment.
Figure 20:
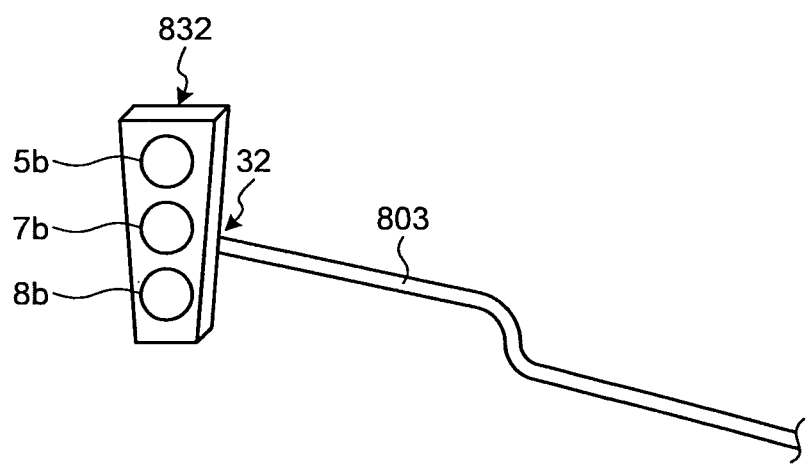
FIG. 20 is a perspective view illustrating a connector portion of a probe base end according to the fifth embodiment.

FIG. 19 is a perspective view as seen from the connector surface of the main unit according to the fifth embodiment. FIG. 20 is a perspective view illustrating the connector portion of the probe base end according to the fifth embodiment.

As illustrated in FIG. 19, in a main unit 802 according to the fifth embodiment, a connector forming portion 840 has a hollow portion 841 formed to have a trapezoidal shape. In addition, as illustrated in FIG. 20, a connector portion 832 of the base end of a probe 803 connected to the main unit 802 is also formed to have a trapezoidal shape to match the shape of the hollow portion 841.

In this manner, according to the fifth embodiment, since the hollow portion 841 of the main unit 802 and the connector portion 832 of the probe 803 have a trapezoidal shape, it is possible to prevent a mistake in the inserting direction of the connector portion 832 of the probe 803.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A probe comprising:
   a plurality of optical fibers that include an irradiation fiber and a light-receiving fiber; and
   an optical member of which a base end face is arranged to abut on leading end faces of the plurality of optical fibers, and a leading end face is exposed outside the probe, wherein
      the leading end face of the optical member is perpendicular to a direction that is parallel to a longitudinal axis of the probe,
      the plurality of optical fibers are arranged such that at least leading end portions of the plurality of optical fibers are parallel with each other,
      a direction that is parallel to longitudinal axes of the leading end portions of the plurality of optical fibers is inclined with respect to a perpendicular line of the leading end face of the optical member such that at least one light beam emitted from a leading end portion of the irradiation fiber travels along a path (i) parallel with the leading end portion of the irradiation fiber and (ii) inclined with respect to the perpendicular line of the leading end face of the optical member, and is incident on the leading end face of the optical member, and
      an inclination angle of the direction that is parallel to the longitudinal axes of the leading end portions of the plurality of optical fibers with respect to the perpendicular line of the leading end face of the optical member is determined based on a numerical aperture of each of the plurality of optical fibers and a refractive index of the optical member in accordance with a formula below:

$$NA/n < \sin\alpha$$

where NA denotes the numerical aperture, n denotes the refractive index, and $\alpha$ denotes the inclination angle.

2. The probe according to claim 1, wherein
   the base end face of the optical member is not in parallel with the leading end face of the optical member,
   each of the leading end faces of the plurality of optical fibers is in parallel with the leading end face of the optical member, and
   a refractive index of the optical member is equal to a refractive index of cores of the plurality of optical fibers.

3. The probe according to claim 1, wherein
   the base end face of the optical member is not in parallel with the leading end face of the optical member, and
   each of the leading end faces of the plurality of optical fibers is in parallel with the base end face of the optical member.

* * * * *